United States Patent
Wang et al.

(10) Patent No.: US 10,601,132 B2
(45) Date of Patent: Mar. 24, 2020

(54) ACTIVE PHASE SWITCHABLE ARRAY

(71) Applicant: NATIONAL SUN YAT-SEN UNIVERSITY, Kaohsiung (TW)

(72) Inventors: Fu-Kang Wang, Kaohsiung (TW); Tzyy-Sheng Horng, Kaohsiung (TW); Lih-Tynh Hwang, Kaohsiung (TW); Chung-Yi Hsu, Kaohsiung (TW); Cho-Ying Chuang, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 298 days.

(21) Appl. No.: 15/695,069

(22) Filed: Sep. 5, 2017

(65) Prior Publication Data
US 2018/0083358 A1   Mar. 22, 2018

Related U.S. Application Data

(63) Continuation-in-part of application No. 15/391,968, filed on Dec. 28, 2016, now Pat. No. 10,413,210.

(30) Foreign Application Priority Data

Sep. 22, 2016   (TW) .............................. 105130608 A
Jul. 7, 2017   (TW) .............................. 106122894 A

(51) Int. Cl.
*H01Q 3/36*   (2006.01)
*H01Q 21/22*   (2006.01)
(Continued)

(52) U.S. Cl.
CPC ............. *H01Q 3/36* (2013.01); *A61B 5/0002* (2013.01); *A61B 5/0004* (2013.01);
(Continued)

(58) Field of Classification Search
CPC ........ H01Q 3/36; H01Q 3/2652; H01Q 21/22; A61B 5/05; A61B 5/7228; A61B 5/7278;
(Continued)

(56) References Cited

U.S. PATENT DOCUMENTS 8,721,554 B2   5/2014   Lin et al.
8,754,772 B2   6/2014   Horng et al.
(Continued)

FOREIGN PATENT DOCUMENTS

TW   201315437   4/2013
WO   2007/101343 A1   9/2007
(Continued)

OTHER PUBLICATIONS

Mu-Cyan Tang et al., A Self- and Mutually Injection-Locked Radar System for Monitoring Vital Signs in Real Time With Random Body Movement Cancellation, IEEE Transactions on Microwave Theory and Techniques, vol. 64, No. 12, Dec. 2016, Nov. 18, 2016, 4812-4822.

(Continued)

*Primary Examiner* — Rex R Holmes
(74) *Attorney, Agent, or Firm* — Jackson IPG PLLC; Demian K. Jackson

(57) ABSTRACT

An active phase switchable array includes a plurality of antenna elements and a bias circuit. Each of the radar elements includes an antenna, a power coupling network and an injection-locked oscillator (ILO), and each of the antenna elements is coupled with each other through the power coupling networks for operating the ILO of each of the antenna elements in self- and mutual-injection-locked states. The antenna elements in self-injection-locked state are utilized to detect the vital signs of subjects, and the antenna elements in mutual-injection-locked state are utilized to produce phase difference between the radiating signals of (Continued)

the antenna elements for forming a beam. As a result, the active phase switchable array can simultaneously detect the vital signs of multiple subjects.

16 Claims, 11 Drawing Sheets

(51) Int. Cl.
| | |
|---|---|
| *G01S 13/88* | (2006.01) |
| *A61B 5/00* | (2006.01) |
| *A61B 5/0205* | (2006.01) |
| *G01S 13/536* | (2006.01) |
| *A61B 5/05* | (2006.01) |
| *G01S 7/03* | (2006.01) |
| *G01S 13/87* | (2006.01) |
| *H01Q 3/26* | (2006.01) |
| *A61B 5/08* | (2006.01) |
| *A61B 5/024* | (2006.01) |
| *G01S 13/58* | (2006.01) |
| *G01S 13/02* | (2006.01) |
| *G01S 13/34* | (2006.01) |

(52) U.S. Cl.
CPC .......... *A61B 5/0205* (2013.01); *A61B 5/0507* (2013.01); *A61B 5/7214* (2013.01); *A61B 5/7225* (2013.01); *A61B 5/7278* (2013.01); *G01S 7/034* (2013.01); *G01S 13/536* (2013.01); *G01S 13/87* (2013.01); *G01S 13/88* (2013.01); *H01Q 3/2652* (2013.01); *H01Q 21/22* (2013.01); *A61B 5/024* (2013.01); *A61B 5/05* (2013.01); *A61B 5/0816* (2013.01); *A61B 5/7228* (2013.01); *A61B 2562/0228* (2013.01); *A61B 2562/04* (2013.01); *G01S 13/34* (2013.01); *G01S 13/583* (2013.01); *G01S 2013/0254* (2013.01)

(58) Field of Classification Search
CPC ... A61B 5/7225; A61B 5/0507; A61B 5/0004; A61B 5/024; A61B 5/0816; A61B 2562/04; A61B 2562/0228; A61B 5/0205; A61B 5/0002; A61B 5/7214; G01S 13/87; G01S 13/536; G01S 7/034; G01S 13/88; G01S 13/583; G01S 2013/0254; G01S 13/34
See application file for complete search history.

(56) References Cited

U.S. PATENT DOCUMENTS

| | | |
|---|---|---|
| 2010/0152600 A1 | 6/2010 | Droitcour et al. |
| 2010/0198083 A1 | 8/2010 | Lin et al. |
| 2012/0146796 A1 | 6/2012 | Margon et al. |
| 2012/0209087 A1 | 8/2012 | Horng et al. |
| 2012/0235689 A1 | 9/2012 | Jau et al. |
| 2014/0128748 A1 | 5/2014 | Horng et al. |
| 2014/0266889 A1 | 9/2014 | Schiller |
| 2015/0018676 A1 | 1/2015 | Barak |
| 2016/0154098 A1 | 6/2016 | Pu et al. |

FOREIGN PATENT DOCUMENTS

| | | |
|---|---|---|
| WO | 2013/118121 A1 | 8/2013 |
| WO | 2014/159773 A1 | 10/2014 |
| WO | 2015/160272 A1 | 10/2015 |
| WO | 2015/174879 A1 | 11/2015 |

OTHER PUBLICATIONS

Jhao-Yun Guo, Study of Self- and Mutually Injection-Locked Radar for Vital Sign Detection with Random Body Movement Cancellation, Master Thesis of National Sun Yat-sen University, Sep. 2, 2016.

Mu-Cyun Tang et al., Same Side Dual SIL-Radar System for Real-Time Vital Sign Monitoring with Random Body Movement Cancellation, Microwave Symposium (IMS), 2016 IEEE MTT-S International, Date of Conference: May 22-27, 2016.

Taiwanese Office Action dated Mar. 1, 2017 for Taiwanese Patent Application No. 105130608, 3 pages.

Chung-Yi Hsu et al., Detection of Vital Signs for Multiple Subjects by Using Self-Injection-Locked Radar and Mutually Injection-Locked Beam Scanning Array, International Microwave Symposium 2017, Jun. 7, 2017.

Fu-Kang Wang et al., A Novel Vital-Sign Sensor Based on a Self-Injection-Locked Oscillator, IEEE Transactions on Microwave Theory And Techniques, vol. 58, No. 12, Dec. 2010, pp. 4112-4120.

Fu-Kang Wang et al., Mutual Injection-Locked SIL Sensor Array for Vital Sign Detection with Random Body Movement Cancellation, 2011 IEEE MTT-S International Microwave Symposium.

Taiwanese Office Action dated Sep. 17, 2018 for Taiwanese Patent Application No. 106122894, 6 pages.

European Search Report dated Dec. 1, 2017 for European Patent Application No. 17170926.4, 10 pages.

ACTIVE PHASE SWITCHABLE ARRAY

RELATED APPLICATIONS

This application is a Continuation in part of U.S. patent application Ser. No. 15/391,968, filed Dec. 28, 2016.

FIELD OF THE INVENTION

This invention generally relates to a phase array, and more particularly to an active phase switchable array.

BACKGROUND OF THE INVENTION

Conventional phase array is applied in communication system or search radar, and includes an antenna array which can increase the signal intensity in a specific direction and decrease the signal intensity in other directions for beamforming by controlling the phase of the signals radiated from each antenna. The beam covering the target communication device or subject can decrease the beam influence on other devices or the influence of environment noise on the phase array for improving the communication or search capability.

With reference to FIG. 1, a passive phase array 200 includes a plurality of antenna elements 210 and a transceiver module 220, wherein the antenna elements 210 are coupled to the transceiver module 220 by a power splitter. Each of the antenna elements 210 includes an antenna 211, an amplifier 212 and a phase shifter 213, wherein each signal is transmitted to each antenna element 210 via the power splitter, then phase-shifted by the phase shifter 213 and amplified by the amplifier 212, and finally radiated from the antenna 211. The phase shifter 213 of each of the antenna elements 210 shifts the phase of each of the signals to stack and cancel the signals with each other for forming a beam. The passive phase array 200 can form the beam with different direction, but this architecture needs more active control elements to control the signals, which increase the power loss, the control complexity and the cost.

SUMMARY

The primary object of the present invention is to produce phase difference between output signals of antenna elements according to the mutual-injection-locked mechanism of the antenna elements to form a beam. And at the same time, each of the antenna elements can operate in self-injection-locked state by self-injection-locked mechanism, and the antenna element in self-injection-locked state is sensitivity to subject's vibration for detecting the vital sign of the subject.

The active phase switchable array of the present invention includes a plurality of antenna elements and a bias circuit. Each of the antenna elements includes an antenna, a power coupling network and an injection-locked oscillator (ILO), wherein the power coupling network is coupled to the antenna and the ILO, an output signal output from the ILO is transmitted to the antenna through the power coupling network. And the antenna is configured to radiate the output signal to a subject, wherein a reflected signal reflected from the subject is received by the antenna and transmitted to the ILO through the power coupling network to allow the ILO to operate in a self-injection-locked state. And the power coupling network of one of the antenna elements is coupled to the power coupling network of the other antenna element, and the output signal from the ILO of the other antenna element is transmitted to the ILO of the antenna element through the power coupling networks to allow the ILO to operate in a mutual-injection-locked state. The bias circuit is configured to output a plurality of modulation voltages, wherein the modulation voltages are respectively transmitted to the ILO of each of the antenna elements to control a free-running frequency of each of the ILOs, and the output signals radiated from the antennas are configured to form a direction adjustable beam.

The active phase switchable array of the present invention can detect the vital sign of the subject by the self-injection-locked mechanism of each of the antenna elements, and can produce the phase difference between the output signals of the antenna elements by the mutual-injection-locked mechanisms of the antenna elements to allow the active phase switchable array possess the capability of the beamforming for detecting the vital signs of multiple subjects simultaneously.

DETAILED DESCRIPTION OF THE INVENTION

Figure 1:
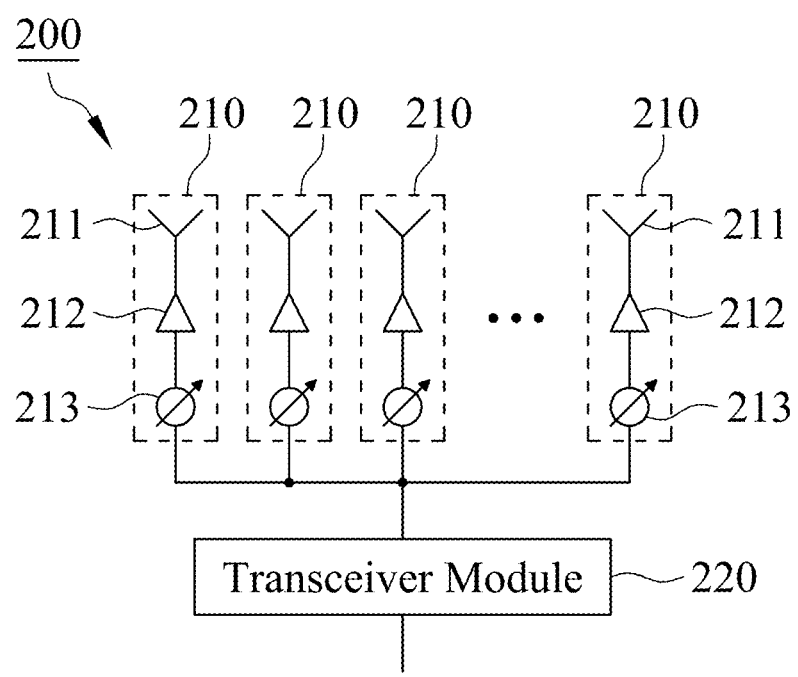
FIG. 1 is a circuit diagram illustrating a conventional passive phased array.
Figure 2:
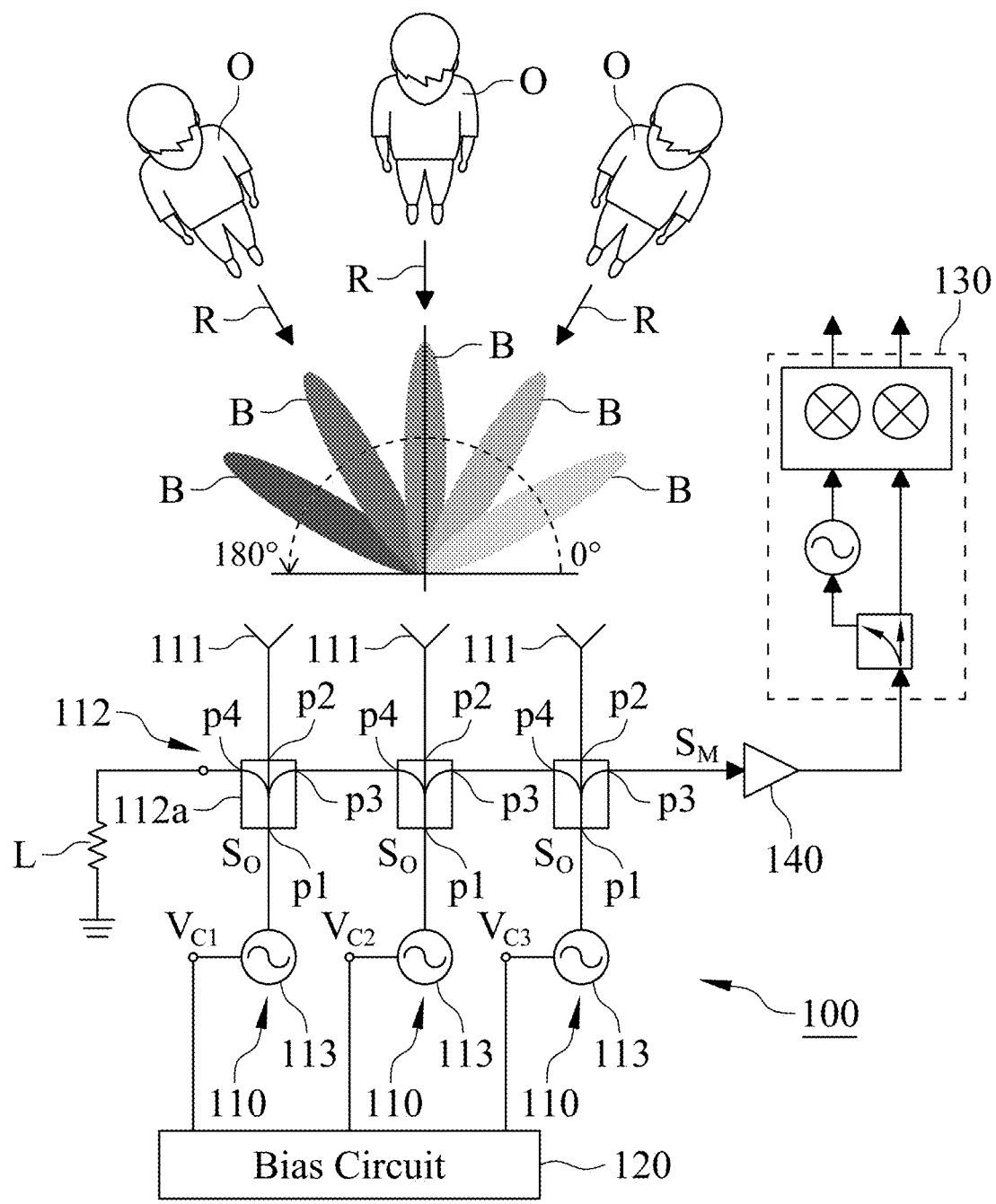
FIG. 2 is a circuit diagram illustrating an active phase switchable array in accordance with a first embodiment of the present invention.

With reference to FIG. 2 which is a circuit diagram of an active phase switchable array 100 in accordance with a first embodiment of the present invention, the active phase switchable array 100 includes a plurality of antenna elements 110, a bias circuit 120, a demodulation circuit 130 and an amplifier 140. The bias circuit 120 is coupled to the antenna elements 110, and the demodulation circuit 130 is coupled to one of the antenna elements 110 through the amplifier 140. In other embodiment, the amplifier 140 is not required when the output power of each of the antenna elements 110 or the sensitivity of the demodulation circuit 130 is high enough.

With reference to FIG. 2, the active phase switchable array 100 has three antenna elements 110 in the first embodiment. In the other embodiment, the active phase switchable array 100 can has two or more than three antenna elements 110. Each of the antenna elements 110 includes an antenna 111, a power coupling network 112 and an injection-locked oscillator (ILO) 113, wherein the power coupling network 112 includes a power splitter 112a having a first port p1, a second port p2, a third port p3 and a fourth port p4. The first port p of the power splitter 112a is coupled to the ILO 113, the second port p2 of the power splitter 112a is coupled to the antenna 111, and the third port p3 of the power splitter 112a is coupled to the fourth port p4 of the other power splitter 112a.

With reference to FIG. 2, the bias circuit 120 is configured to output a plurality of individual modulation voltages $V_{C1}$, $V_{C2}$ and $V_{C3}$ to the ILO 113 of each of the antenna elements 110 for controlling a free-running frequency of each of the ILOs 113. An output signals $S_O$ is output from each of the ILOs 113 is transmitted to the antenna 111 via the power splitter 112a, and radiated from the antenna 111 to a subject O. A reflected signal R is reflected from the subject O, wherein the reflected signal R is received by each of the antennas 111 and transmitted to the ILOs 113 through the power coupling network 112 to allow the ILOs 113 operate in a self-injection-locked (SIL) state. Furthermore, owing to the power splitters 112a are coupled to each other, the output signals $S_O$ of one of the ILOs 113 is transmitted to the other ILO 113 through the power splitter 112a and the other power splitter 112a to allow the other ILO 113 to operate in a mutual-injection-locked (MIL) state.

With reference to FIG. 2, there is a phase difference between the output signals $S_O$ of the ILOs 113 caused by the self- and mutual-injection-locked mechanisms of the ILOs 113, and a direction adjustable beam B is formed when the antennas 111 radiate the output signals $S_O$. For this reason, the bias circuit 120 is provided to control the free-running frequency of each of the output signals $S_O$ to change the direction of the beam B for detecting multiple subjects O.

Figure 3:
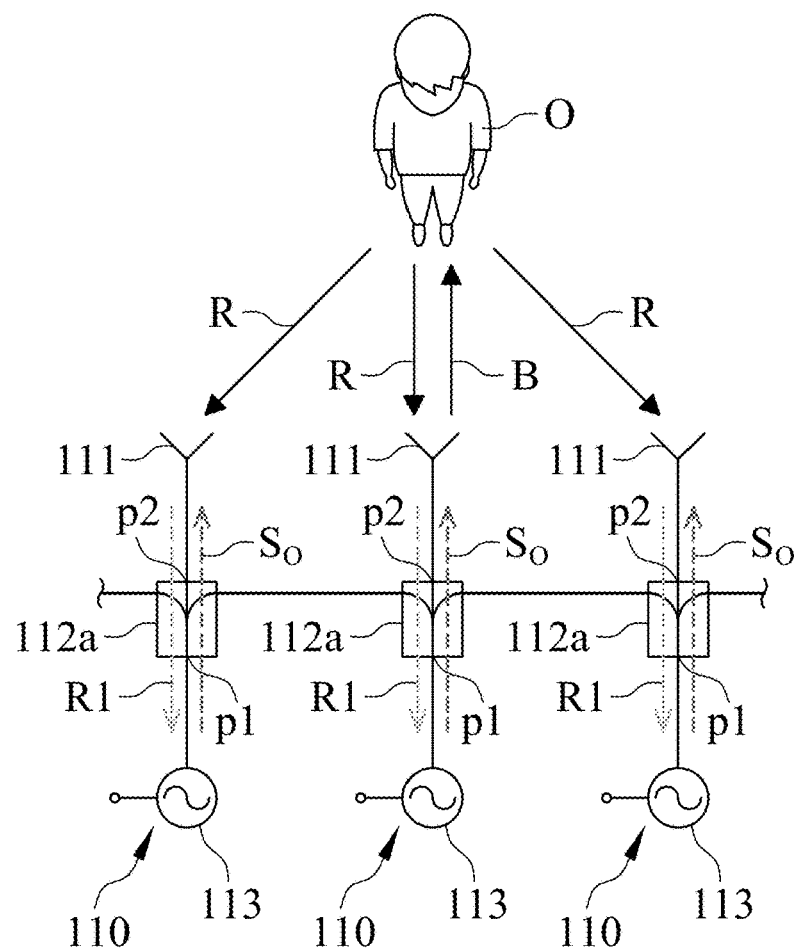
FIG. 3 is a circuit diagram illustrating self-injection-locked (SIL) paths of antenna elements in accordance with the first embodiment of the present invention.

With reference to FIG. 3 which shows the SIL path of the ILOs 113 in the first embodiment, the output signals $S_O$ from each of the ILOs 113 is transmitted to the first port p1 of each of the power splitters 112a, and then transmitted to each of the antennas 110 from the second port p2 of each of the power splitters 112a. Each of the antennas 111 radiates the output signals $S_O$, and the beam B formed by the output signals $S_O$ is radiated toward the subject O to allow the subject O to reflect the reflected signal R, wherein the reflected signal R contains Doppler shift components caused by the vital sign of the subject O. The reflected signal R is received by the antennas 111, and then received by the second port p2 of each of the power splitters 112a. At last, the reflected signal R is output from the first port p1 of each of the power splitters 112a, and injected into each of the ILOs 113 to frequency modulate the output signals $S_O$ of each of the ILOs 113. As a result, the ILOs 113 operate in the SIL state, and the vital sign of the subject O can be obtained by frequency demodulation of the output signals $S_O$ from the ILOs 113 and spectrum analysis.

Figure 4:
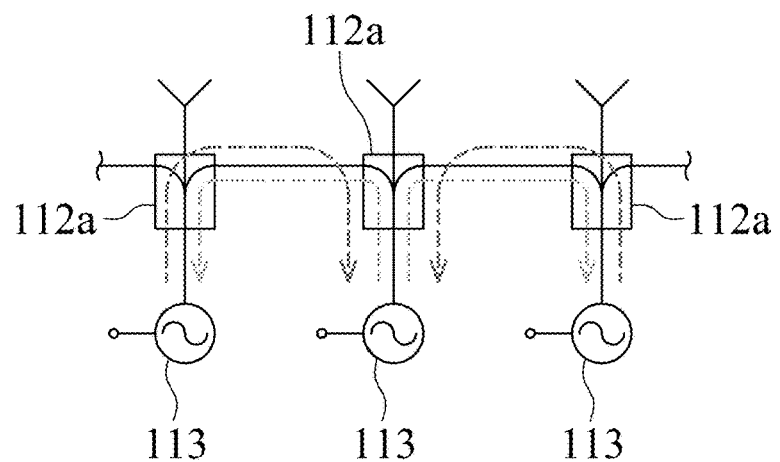
FIG. 4 is a circuit diagram illustrating mutual-injection-locked (MIL) paths of antenna elements in accordance with the first embodiment of the present invention.

With reference to FIG. 4, it represents the MIL path of the ILOs 113 in the first embodiment. For simplicity, only the left and middle antenna elements 110 are used to explain the MIL path below. The output signals $S_O$ from the left ILO 113 is injected to the middle ILO 113 by the left and middle power splitters 112a, and the output signals $S_O$ from the middle ILO 113 is also injected to the left ILO 113 via the middle and left power splitters 112a to allow the ILOs 113 to operate in the MIL state. The mutual-injection-locked mechanism between the ILOs 113 can change the phase difference between the output signals $S_O$ of the ILOs 113, so the active phase switchable array 100 without moving can perform beamforming to scan multiple subjects O for obtaining their vital signs.

With reference to FIG. 2, the demodulation circuit 130 is coupled to the third port p3 of the rightmost power splitter 112a for receiving a frequency modulation signal $S_M$, and the fourth port p4 of the leftmost power splitter 112a is, but not limited to, coupled to a load matching L. In other embodiment, the fourth port p4 of the leftmost power splitter 112a can be also coupled to the demodulation circuit 130 to allow the demodulation circuit 130 to receive a further frequency modulation signal for frequency demodulation and to reduce the usage amount of power splitters and low noise amplifiers in the demodulation circuit 130. In the first embodiment, the frequency modulation signal $S_M$ is the output signals $S_O$ of the rightmost antenna element 110. Because the ILO 113 of the rightmost antenna element 110 is also self-injection-locked by the reflected signal R, the frequency modulation signal $S_M$ received by the demodulation circuit 130 contains the Doppler phase shift caused by the vibration of the subject O, and the vibration information of the subject O can be obtained through the processing and analysis of the frequency modulation signal $S_M$ by the demodulation circuit 130 to detecting the vital signs of the subject O. In the first embodiment, the demodulation circuit 130 is a delay line frequency discriminator.

Figure 5:
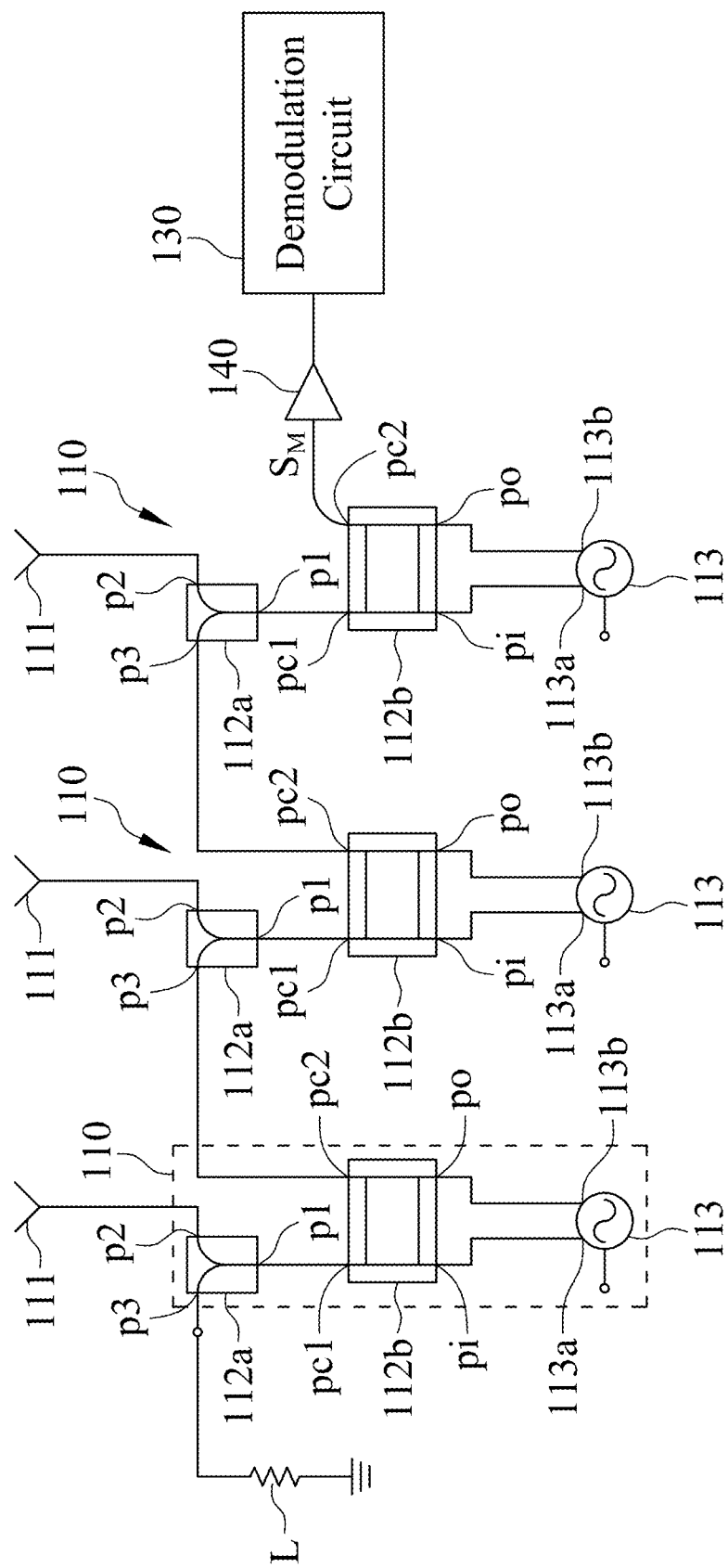
FIG. 5 is a circuit diagram illustrating an active phase switchable array in accordance with a second embodiment of the present invention.

With reference to FIG. 5, it represents a second embodiment of the present invention, and the difference between the first and second embodiments is that the power coupling network 112 of each of the antenna elements 110 includes a power splitter 112a and a direction coupler 112b in the second embodiment. The direction coupler 112b includes an input port pi, an output port po, a first coupling port pc1 and a second coupling port pc2, and the power splitter 112a includes a first port p1, a second port p2 and a third port p3. The input port pi is coupled to a signal output port 113a of the ILO 113, the output port po is coupled to an injection port 113b of the ILO 113, the first coupling port pc1 is coupled to the first port p1 of the power splitter 112a, the second port p2 of the power splitter 112a is coupled to the antenna 111, and the second coupling port pc2 of the direction coupler 112b is coupled to the third port p3 of the other power splitter 112a.

Figure 6:
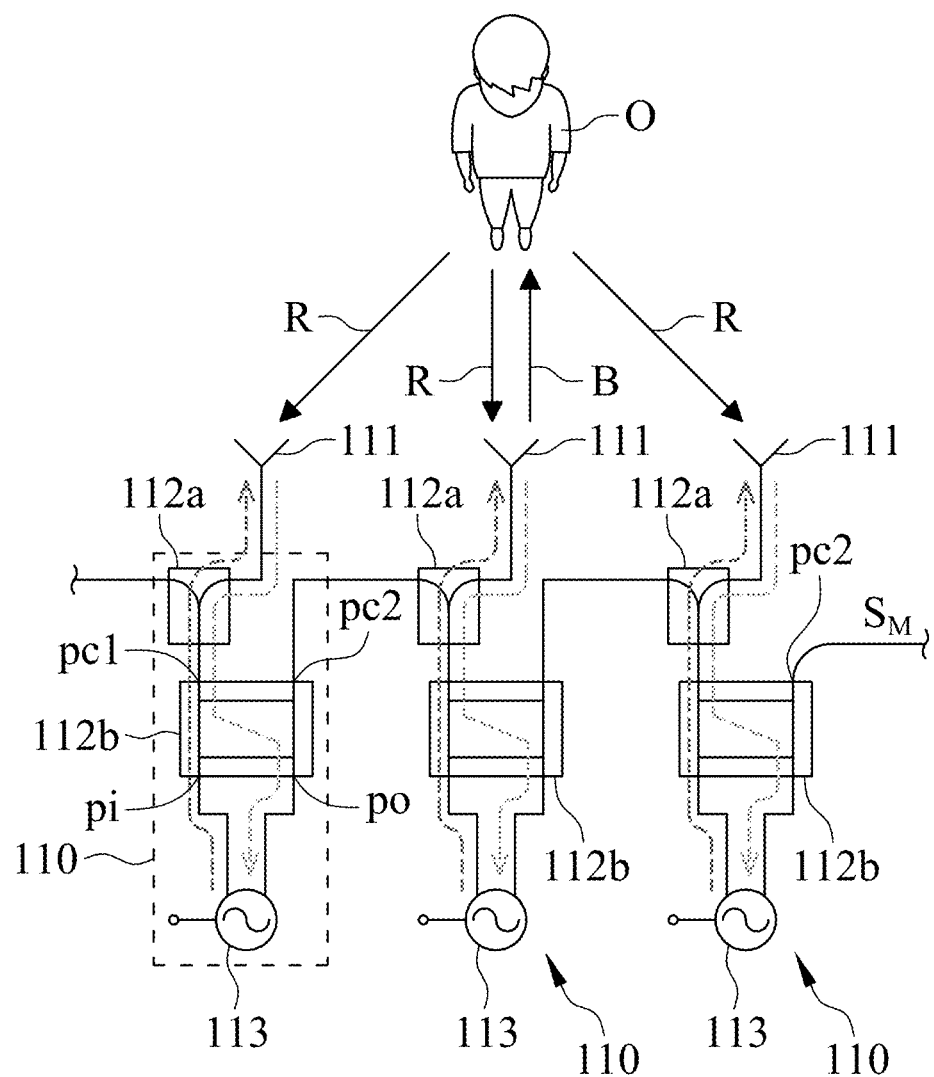
FIG. 6 is a circuit diagram illustrating self-injection-locked (SIL) paths of antenna elements in accordance with the second embodiment of the present invention.

FIG. 6 is a diagram illustrating the SIL path of the ILOs 113 in the second embodiment. Each of the ILOs 113 is configured to output the output signal $S_O$ to the input port pi of the directional coupler 112b via the signal output port 113a. The output signal $S_O$ is output from the first coupling port pc1 and transmitted to the antenna 111 through the power splitter 112a, and the antennas 111 are configured to radiate the output signals $S_O$ and form a beam B to the subject O. A reflected signal R is reflected form the subject O and received by the antennas 111. And the reflected signal R is transmitted to the first coupling port pc1 of the direction coupler 112b via the power splitter 112a, then output from the output port po, and finally injected into the injection port 113b of each of the ILOs 113 to lead the ILOs 113 operated in the SIL state. In the second embodiment, the demodulation circuit 130 is coupled to the second coupling port pc2 of the rightmost direction coupler 112b for receiving a frequency modulation signal $S_M$. The demodulation circuit 130 can demodulate the frequency modulation signal $S_M$ to obtain the vital signs of the subject O because the reflected signal R contains the Doppler phase shift caused by the vibration of the subject O. Furthermore, the third port p3 of the leftmost power splitter 112a is, but not limited to, coupled to a load matching L. In other embodiment, the third port p3 of the leftmost power splitter 112a also can be coupled to the demodulation circuit 130, and the demodulation circuit 130 can receive a further frequency modulation signal for frequency demodulation, and the usage amount of power splitters and low noise amplifiers can be reduced.

Figure 7:
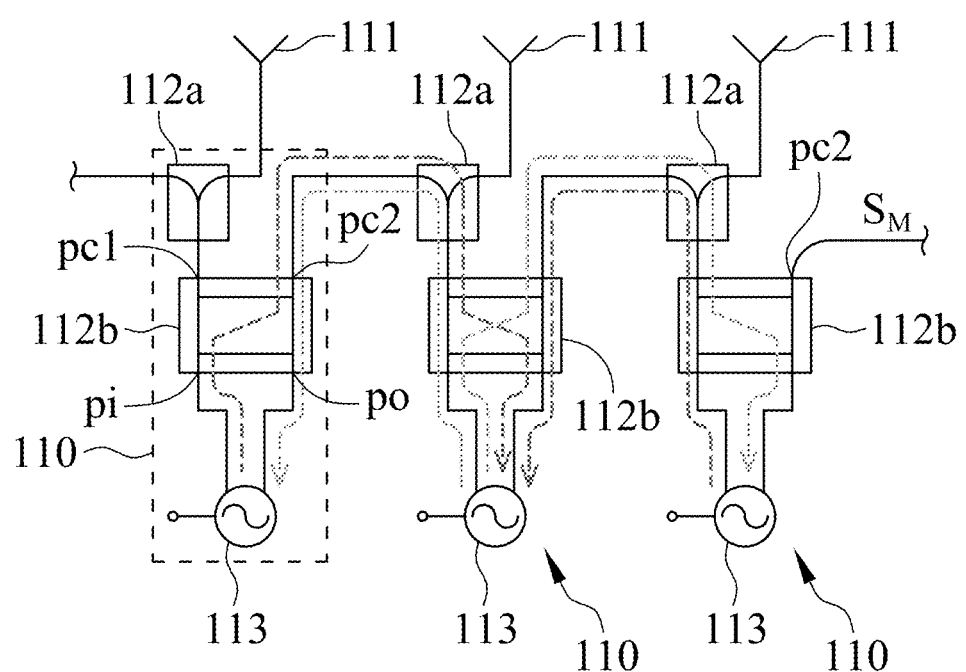
FIG. 7 is a circuit diagram illustrating mutual-injection-locked (MIL) paths of antenna elements in accordance with the second embodiment of the present invention.

With reference to FIG. 7, it is a diagram representing the MIL path of the ILOs 113 in the second embodiment. For simplicity, only the left and middle antenna elements 110 are used to explain the MIL path below. The output signals $S_O$ of the left ILO 113 is input to the input port pi of the left directional coupler 112b and output to the power splitter 112a of the middle antenna element 110 from the second coupling port pc2 of the left directional coupler 112b. And finally the output signal $S_O$ of the left ILO 113 is injected into the middle ILO 113 through the middle direction coupler 112b. Correspondingly, the output signals $S_O$ from the middle ILO 113 also can be injected into the left ILO 113 through the middle direction coupler 112b, the middle power splitter 112a and the left directional coupler 112b to lead all of the ILOs 113 are operated in the MIL state. The mutual-injection-locked mechanism of the ILOs 113 can change the phase difference between the output signals $S_O$ of the ILOs 113 to allow the active phase switchable array 100 to be able of beamforming. For this reason, the active phase switchable array 100 without displacement can scan multiple subjects O. In the second embodiment, the direction coupler 112b is a hybrid direction coupler, and the phase difference between the first coupling port pc1 and the second coupling port pc2 of the directional coupler 112b is 90° which can produce the phase difference between the output signals $S_O$ of the ILOs 113.

Figure 8:
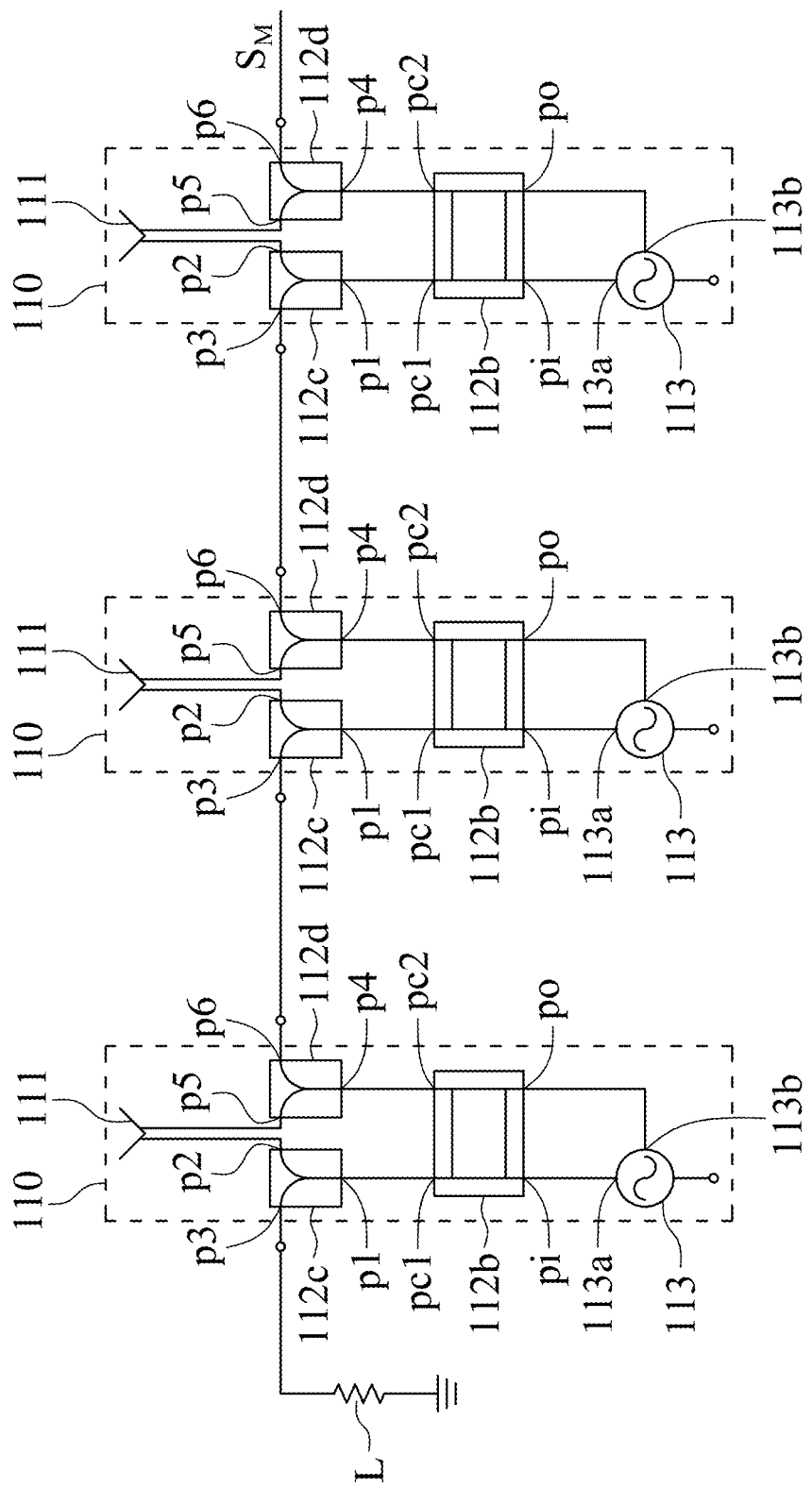
FIG. 8 is a circuit diagram illustrating an active phase switchable array in accordance with a third embodiment of the present invention.

With reference to FIG. 8 which illustrates a third embodiment of the present invention, the difference between the first and third embodiments is the power coupling network 112 of each of the antenna elements 110 includes a direction coupler 112b, a first power splitter 112c and a second power splitter 112d in the third embodiment. The direction coupler 112b includes a input port pi, a output port po, a first coupling port pc1 and a second coupling port pc2, the first power splitter 112c includes a first port p1, a second port p2 and a third port p3, and the second power splitter 112d includes a fourth port p4, a fifth port p5 and a sixth port p6. The input port pi is coupled to a signal output port 113a of the ILO 113, the output port po is coupled to an injection port 113b of the ILO 113, the first coupling port pc1 is coupled to the first port p1 of the first power splitter 112c, the second port p2 of the first power splitter 112c is coupled to the antenna 111, the third port p3 of the first power splitter 112c is coupled to a load matching L, the second coupling port pc2 of the direction coupler 112b is coupled to the fourth port p4 of the second power splitter 112d, the fifth port p5 of the second power splitter 112d is coupled to the antenna 111, and the sixth port p6 of the second power splitter 112d is coupled to the third port p3 of the other first power splitter 12c.

Figure 9:
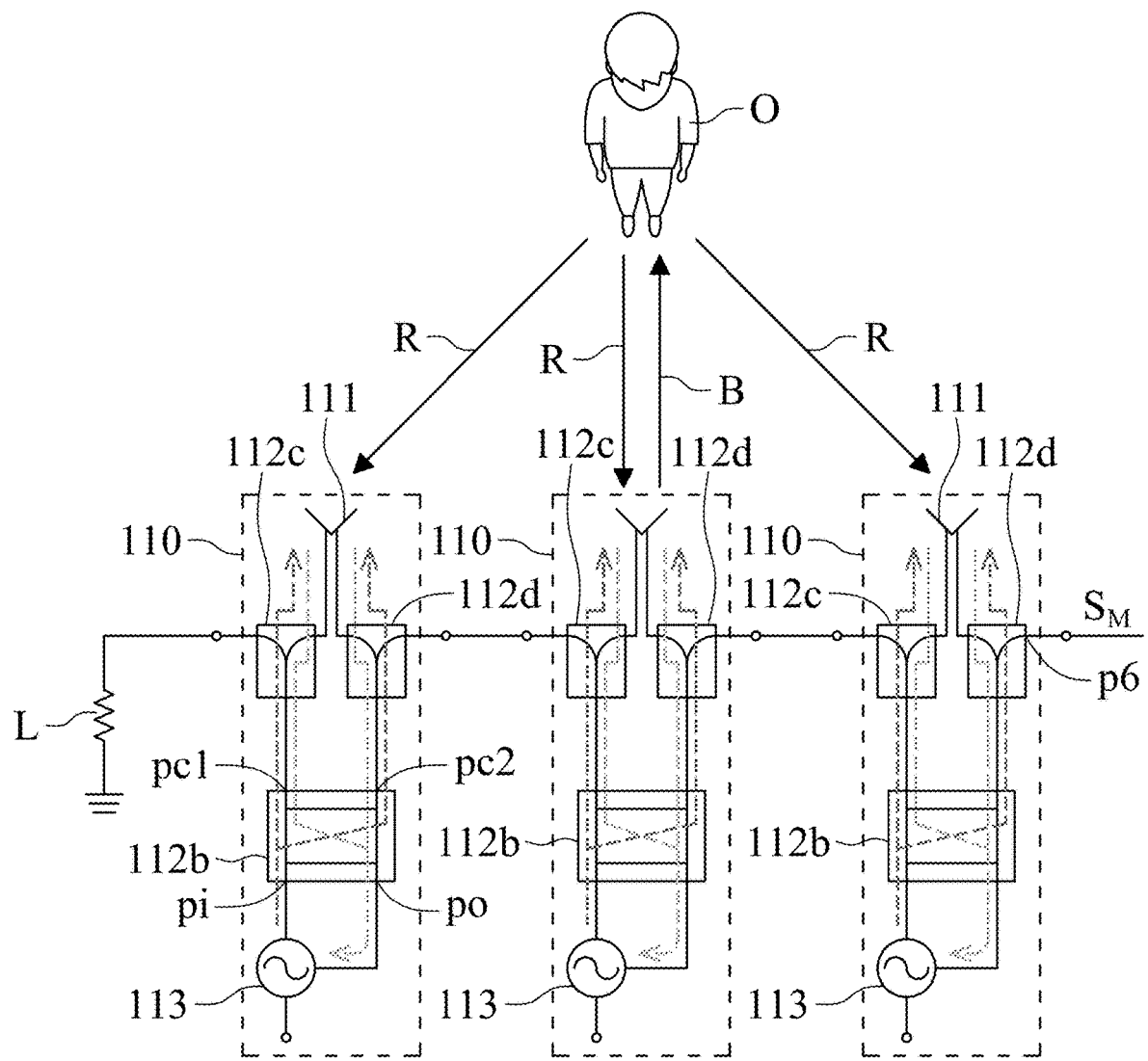
FIG. 9 is a circuit diagram illustrating self-injection-locked (SIL) paths of antenna elements in accordance with the third embodiment of the present invention.

With reference to FIG. 9, it represents the SIL path of the ILOs 113 of the third embodiment. The signal output port 113a of each of the ILOs 113 outputs the output signal $S_O$ to the input port pi of the directional coupler 112b, then the output signals $S_O$ is output from the first coupling port pc1 and the second coupling port pc2, and transmitted to the antenna 111 through the first power splitter 112c and the second power splitter 112d. The antennas 111 radiate the output signals $S_O$ and form a beam B toward the subject O, wherein a reflected signal R is reflected from the subject O. The reflected signal R is received by the antennas 111, and transmitted to the first coupling port pc1 and the second coupling port pc2 of the directional coupler 112b through the first power splitter 112c and the second power splitter 112d respectively, and then output form the output port po. Lastly the reflected signal R is injected into the injection port 113b of each of the ILOs 113 to allow the ILOs 113 operated in the SIL state. In the third embodiment, the demodulation circuit 130 is coupled to the sixth port p6 of the second power splitter 112d of the rightmost directional coupler 112b for receiving a frequency modulation signal $S_M$. The demodulation circuit 130 is able to demodulate the frequency modulation signal $S_M$ to obtain the vital sign of the subject O owing to the reflected signal R contains the Doppler phase shift caused by the vibration of the subject O. In other embodiment, the demodulation circuit 130 can be coupled to the third port p3 of the leftmost first power splitter 112c to receive and demodulate a further frequency modulation signal for reducing the usage amount of power splitters and low noise amplifiers in the demodulation circuit 130.

With reference to FIG. 9, the output signals $S_O$ of each of the antenna elements 110 which transmitted through the directional coupler 112b, the first power splitter 112c and the second power splitter 112d is divided into two output signals $S_O$ with 90° phase difference. The two output signals $S_O$ in quadrature with each other are fed to the antenna 111 for radiating left-hand circularly polarized wave to the subject O, and right-hand circularly polarized wave is reflected from the subject O toward each of the antennas 111 for effectively achieving spatial polarization diversity and improving system sensitivity.

Figure 10:
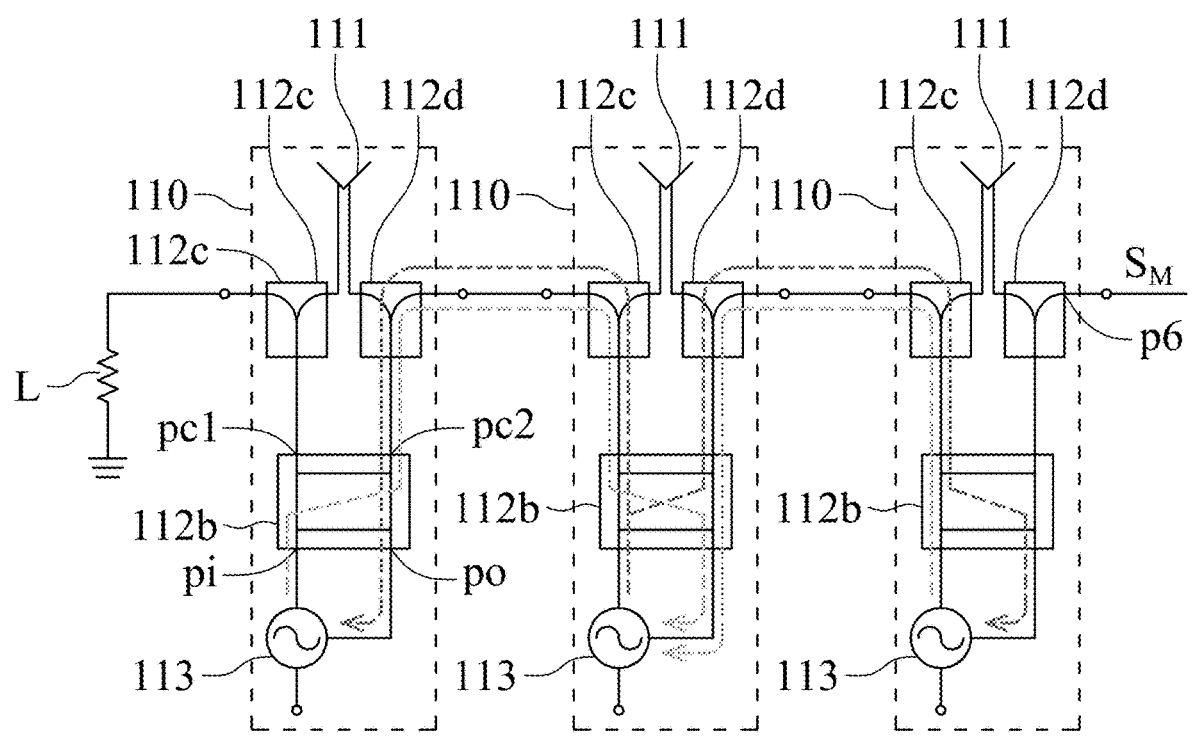
FIG. 10 is a circuit diagram illustrating mutual-injection-locked (MIL) paths of antenna elements in accordance with the third embodiment of the present invention.

With reference to FIG. 10 which is provided to illustrate the MIL path of the ILOs 113 in the third embodiment. For simplicity, only the left and middle antenna elements 110 are used to explain the MIL path below. The output signals $S_O$ of the left ILO 113 is input to the input port pi of the left directional coupler 112b and output to the left second power splitter 112d through the second coupling port pc2, then injected into the middle ILO 113 via the middle first power splitter 112c and the middle directional coupler 112b. Moreover, the output signal $S_O$ of the ILO 113 of the middle antenna element 110 is also injected into the left ILO 113 through the middle directional coupler 112b, the middle first power splitter 112c, the left second power splitter 112d and the left directional coupler 112b. As a result, all of the ILOs 113 are operated in the MIL state. The mutual-injection-locked among the ILOs 113 can vary the phase difference between the output signals $S_O$ of the ILOs 113 to allow the active phase switchable array 100 to have the advantage of beamforming. Consequently the active phase switchable array 100 seated in fixed position can scan multiple subjects O.

Figure 11:
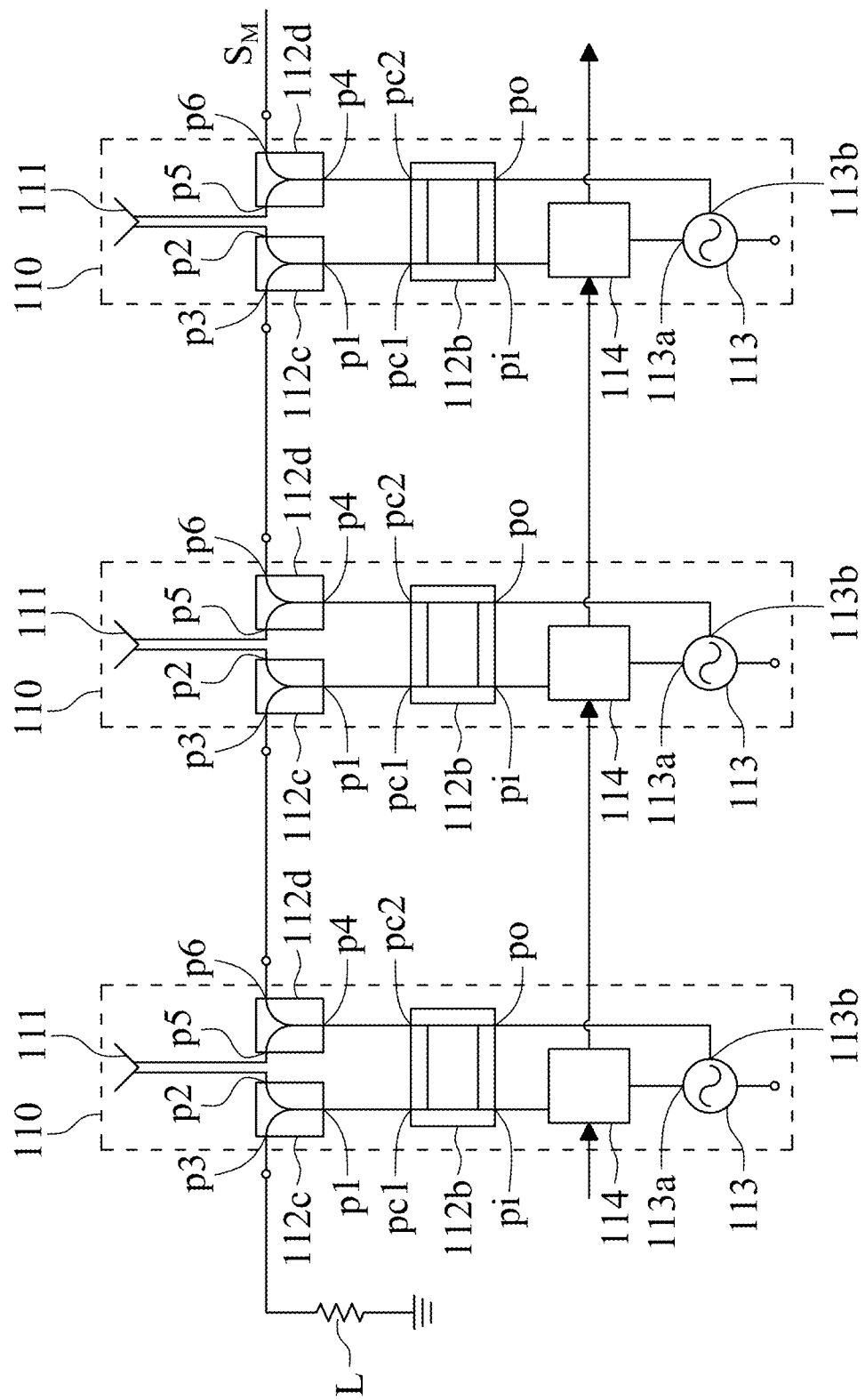
FIG. 11 is a circuit diagram illustrating an active phase switchable array in accordance with a fourth embodiment of the present invention.

A fourth embodiment is represented in FIG. 11. The difference between the third and fourth embodiments is that each of the antenna elements 110 includes a voltage controlled phase shifter 114 in the fourth embodiment. The voltage controlled phase shifter 114 of each of the antenna elements 110 is coupled to the signal output port 113a of the ILO 113 and the input port pi of the directional coupler 112b to phase shift the output signal $S_O$ from the ILO 113 of each of the antenna elements 110 respectively. In the fourth embodiment, the voltage controlled phase shifter 114 is configured to provide the phase difference of (N−1)×±90° for Nth antenna element 110. As a result, the maximum phase difference between the neighbor antenna elements 110 is 360° for improving the scan range of the active phase switchable array 100. And the voltage controlled phase shifter 114 can scan and compare the pole and zero of the antenna patterns at different azimuth angles to enhance the azimuth resolution according to the technology of sum-difference pattern.

Figure 12A:
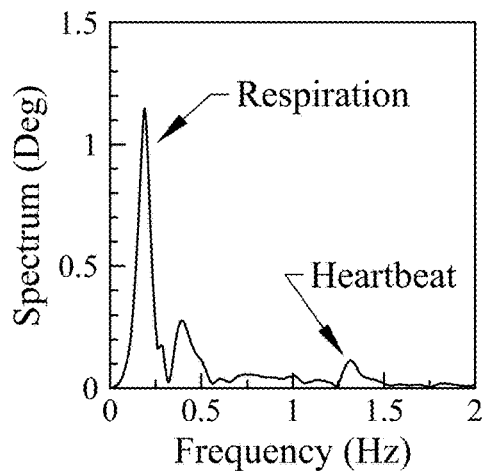
FIGS. 12a to 12c are vital sign detection results of three subjects side by side using the active phase switchable array of the present invention.
Figure 12B:
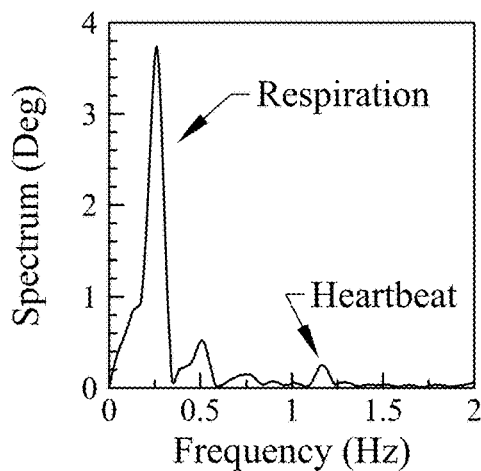
Figure 12C:
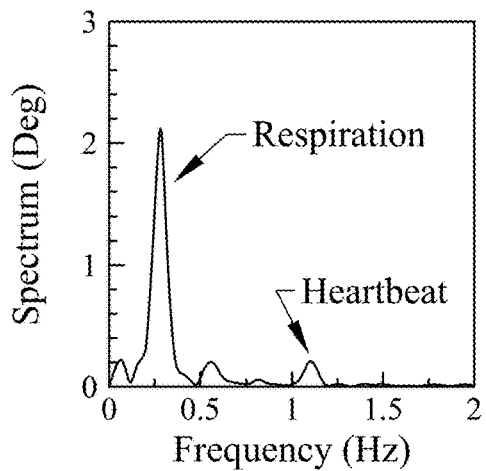

With reference to FIGS. 12a to 12c, these are the experimental results of the active phase switchable array 100 of the present invention for three subjects side by side, wherein the subjects are located within the scan range and spaced apart a distance of one meter. The phase-shift components caused by respiration and heartbeat of the subjects are distinctly represented in FIGS. 12a to 12c, and these results can actually prove that the active phase switchable array 100 of the present invention provides the advantage of detecting the vital signs of multiple subjects simultaneously.

The active phase switchable array 100 of the present invention can detect the vital signs of the subject by the self-injection-locked mechanism of each of the antenna elements 110, and can produce the phase difference between the output signals $S_O$ of the antenna elements 110 by the mutual-injection-locked mechanisms of the antenna elements 110 to allow the active phase switchable array 100 possess the capability of the beamforming to detect the vital signs of multiple subjects simultaneously.

The scope of the present invention is only limited by the following claims. Any alternation and modification without departing from the scope and spirit of the present invention will become apparent to those skilled in the art.

What is claimed is:

1. A active phase switchable array comprising:
   a plurality of antenna elements each including an antenna, a power coupling network and an injection-locked oscillator (ILO), wherein the power coupling network is coupled to the antenna and the ILO, an output signal output from the ILO is configured to transmit to the antenna through the power coupling network, and the antenna is configured to radiate the output signal to a subject, wherein a reflected signal reflected from the subject is received by the antenna and transmitted to the ILO through the power coupling network to allow the ILO to operate in a self-injection-locked state, and wherein the power coupling network of one of the antenna elements is coupled to the power coupling network of another of the antenna elements, and the output signal from the ILO of the another of the antenna elements is transmitted to the ILO of the antenna element through the power coupling networks to allow the ILOs to operate in a mutual-injection-locked state; and
   a bias circuit configured to output a plurality of modulation voltages, wherein the modulation voltages are respectively transmitted to the ILO of each of the antenna elements to control a free-running frequency of each of the ILOs, and a plurality of wireless signals radiated from the antennas are configured to form a direction adjustable beam.

2. The active phase switchable array in accordance with claim 1, wherein the power coupling network of each of the antenna elements includes a power splitter which includes a first port, a second port, a third port and a fourth port, and wherein the first port of the power splitter is coupled to the ILO, the second port of the power splitter is coupled to the antenna, and the third port of the power slitter is coupled to the fourth port of the other power splitter of another of the antenna elements.

3. The active phase switchable array in accordance with claim 2 further comprises a demodulation circuit, wherein the demodulation circuit is coupled to the third port of one of the power splitters for receiving a frequency modulation signal, and the demodulation circuit is configured to demodulate the frequency modulation signal for obtaining a vital sign signal.

4. The active phase switchable array in accordance with claim 3, wherein the demodulation circuit is simultaneously coupled to the fourth port of the power splitter of another of the antenna elements for receiving a further frequency modulation signal, and the demodulation circuit is configured to demodulate by using the two frequency modulation signals.

5. The active phase switchable array in accordance with claim 1, wherein the power coupling network of each of the antenna elements includes a directional coupler and a power splitter, the directional coupler includes a input port, a output port, a first coupling port and a second coupling port, and the power splitter includes a first port, a second port and a third port, wherein the input port is coupled to a signal output port of the ILO, the output port is coupled to an injection port of the ILO, the first coupling port is coupled to the first port of the power splitter, the second port of the power splitter is coupled to the antenna, and the second coupling port of the directional coupler is coupled to the third port of the power splitter of another of the antenna elements.

6. The active phase switchable array in accordance with claim 5 further comprises a demodulation circuit, wherein the demodulation circuit is coupled to the second coupling port of one of the directional couplers for receiving a frequency modulation signal, and the demodulation circuit is configured to demodulate the frequency modulation signal for obtaining a vital sign signal.

7. The active phase switchable array in accordance with claim 6, wherein the demodulation circuit is simultaneously coupled to the third port of the power splitter of another antenna elements for receiving a further frequency modulation signal, and the demodulation circuit is configured to demodulate by using the two frequency modulation signals.

8. The active phase switchable array in accordance with claim 1, wherein the power coupling network of each of the antenna elements includes a directional coupler, a first power splitter and a second power splitter, the directional coupler includes a input port, a output port, a first coupling port and a second coupling port, the first power splitter includes a first port, a second port and a third port, and the second power splitter includes a fourth port, a fifth port and a sixth port, wherein the input port is coupled to a signal output port of the ILO, the output port is coupled to an injection port of the ILO, the first coupling port is coupled to the first port of the first power splitter, the second port of the first power splitter is coupled to the antenna, the second coupling port of the directional coupler is coupled to the fourth port of the second power splitter, the fifth port of the second power splitter is coupled to the antenna, and the sixth port of the second power splitter is coupled to the third port of another of the first power splitters.

9. The active phase switchable array in accordance with claim 8 further comprises a demodulation circuit, wherein the demodulation circuit is coupled to the sixth port of one of the second power splitters for receiving a frequency modulation signal, and the demodulation circuit is configured to demodulate the frequency modulation signal for obtaining a vital sign signal.

10. The active phase switchable array in accordance with claim 9, wherein the demodulation circuit is simultaneously coupled to the third port of the first power splitter of another antenna elements for receiving a further frequency modulation signal, and the demodulation circuit is configured to demodulate using the two frequency modulation signals.

11. The active phase switchable array in accordance with claim 8, wherein each of the antenna elements includes a voltage controlled phase shifter which is coupled to the signal output port of the ILO and the input port of the directional coupler, and the voltage controlled phase shifter is configured to respectively phase shift the output signal output from the ILO of each of the antenna elements.

12. The active phase switchable array in accordance with claim 5, wherein the directional coupler is a hybrid directional coupler.

13. The active phase switchable array in accordance with claim 8, wherein the directional coupler is a hybrid directional coupler.

14. The active phase switchable array in accordance with claim 1, wherein the power coupling network of one of the antenna elements is coupled to a load matching.

15. The active phase switchable array in accordance with claim 5, wherein the power coupling network of one of the antenna elements is coupled to a load matching.

16. The active phase switchable array in accordance with claim 8, wherein the power coupling network of one of the antenna elements is coupled to a load matching.

* * * * *